United States Patent [19]
Orlek et al.

[11] Patent Number: 5,863,952
[45] Date of Patent: Jan. 26, 1999

[54] ENANTIOMERS OF 1-(3,4-DICHLOROBENZYL)-2-METHYLAMINOINDANE

[75] Inventors: Barry Sidney Orlek, Epping; John David Harling, Harlow, both of England

[73] Assignee: SmithKline Beecham plc, Brentford, United Kingdom

[21] Appl. No.: 860,764

[22] PCT Filed: Jan. 10, 1996

[86] PCT No.: PCT/EP96/00206

§ 371 Date: Jun. 11, 1997

§ 102(e) Date: Jun. 11, 1997

[87] PCT Pub. No.: WO96/21641

PCT Pub. Date: Jul. 18, 1996

[30] Foreign Application Priority Data

Jan. 13, 1995 [GB] United Kingdom .................. 9500691

[51] Int. Cl.$^6$ ........................ A61K 31/135; C07C 211/42
[52] U.S. Cl. ........................ 514/657; 514/648; 564/304; 564/315; 564/425
[58] Field of Search ................. 564/304, 315, 564/425; 514/648, 657

[56] References Cited

U.S. PATENT DOCUMENTS 5,639,913  6/1997  Lidor et al. .......................... 564/304

FOREIGN PATENT DOCUMENTS 95 04027  2/1995  WIPO .

*Primary Examiner*—Richard L. Raymond
*Attorney, Agent, or Firm*—Wayne J. Dustman; Charles M. Kinzig

[57] ABSTRACT

The single enantiomers of formula (I) and salts thereof

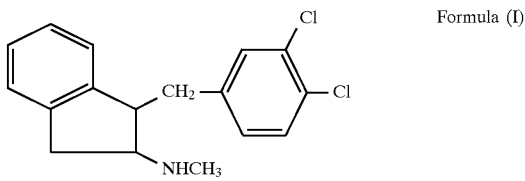

Formula (I)

are calcium channel antagonists useful in the treatment of ischaemic conditions e.g., stroke.

10 Claims, No Drawings

ENANTIOMERS OF 1-(3,4-DICHLOROBENZYL)-2-METHYLAMINOINDANE

This application is a §371 application of PCT/EP96/00206, filed Jan. 10, 1996.

The present invention relates to carbocyclic derivatives, processes for their preparation, pharmaceutical compositions containing them and their use in therapy, in particular as calcium channel antagonists, e.g. for the treatment of ischaemic stroke.

Stroke is reportedly the third most common cause of death in the developed world. Current therapies for ischaemic stroke are limited and have a number of disadvantages, such as the risk of exacerbating haemorrhage. There is therefore a need for new and improved treatments for ischaemic stroke.

EPA 303961 describes compounds of the formula

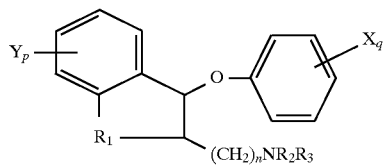

wherein $R_1$ is $C_{1-3}$ alkylene, n and p are each inter alia zero, $R_2$ and $R_3$ represent inter alia hydrogen or lower alkyl, X is inter alia lower alkyl, lower alkoxy, $CF_3$ or halogen and q is zero, 1 or 2. The compounds are said to be useful as antidepressants and as inhibitors of synaptic norepinephrine and serotonin uptake.

EPA 371508 describes similar compounds of the formula:

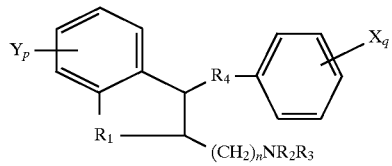

wherein $R_1$, $R_2$, $R_3$, n, p, q and X may have the values recited hereinabove and $R_4$ is oxy or thio, which compounds are said to be useful for the treatment of drug-resistant malaria and other drug-resistant protozoal infections.

Our International Patent application PCT/EP94/02410 (filed 21 Jul. 1994) describes compounds of formula (I):

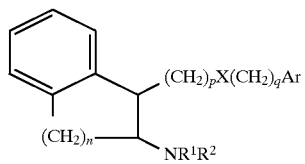

Formula (A)

wherein:
X represents O, S, NH or a bond;
p and q independently represent 0–4 such that the sum of p+q is at least 1;
$R^1$ and $R^2$ each independently represent hydrogen, $C_{1-6}$alkyl, $C_{3-6}$cycloalkyl, or $C_{1-4}$alkyl-$C_{3-6}$cycloalkyl;
n is 1, 2 or 3; and
Ar represents phenyl optionally substituted by 1 to 3 substituents selected from:
halo, $C_{1-4}$alkyl, $C_{1-4}$alkoxy, $C_{1-2}$alkylenedioxy, trifluoromethyl, trifluoromethoxy, CN, $NO_2$, amino, mono- or di- alkylamino, optionally substituted benzoyl and $Ph(CH_2)_rY(CH_2)_s$— where Ph is optionally substituted phenyl, Y is oxygen or a bond and r and s each independently represent 0–4 provided that the sum of r+s is not greater than 4, or
Ar represents an optionally substituted unsaturated monocyclic heteroaryl ring system containing 5 or 6 ring members, or an optionally substituted, unsaturated or partially saturated bicyclic aryl or heteroaryl ring system containing 8–10 ring members,
and salts thereof.

The compounds of formula (A) contain two asymmetric centres; such compounds can exist in diastereomeric forms (cis and trans), each of which can exist as optical isomers (enantiomers). In relation to the diastereoisomers, the substituents on the carbocyclic (e.g. indane) nucleus may both lie on the same side with respect to the plane of the ring (cis-configuration) or on opposite sides (trans-configuration).

The specific examples of formula (A) described in PCT/EP94/02410 include the compound:
(±)cis-1-(3,4-dichlorobenzyl)-2-methylaminoindane (as the hydrochloride salt), which is a mixture of enantiomers.

The present invention now provides the specific enantiomers of this compound, namely:
(+)cis-1-(3,4-dichlorobenzyl)-2-methylaminoindane; and
(−)cis-1-(3,4-dichlorobenzyl)-2-methylaminoindane,
and salts thereof.

Both enantiomers may conveniently be represented by the structural formula (I):

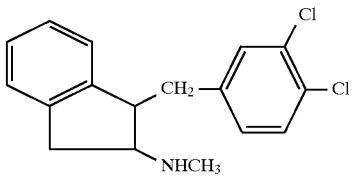

Formula (I)

It will be appreciated that this single formula is not intended to represent a mixture of enantiomers, but each individual enantiomer.

It will also be appreciated that an enantiomer according to the present invention, for example a (+)- enantiomer, will be substantially free from the corresponding (−) enantiomer, and vice versa. Preferably, a specific enantiomer of the invention will contain less than 10%, eg less than 5% and advantageously less than 1%, eg less than 0.5%, of its opposite enantiomer.

For the avoidance of doubt, formulae (I), (II) and (III) depicted herein are intended to represent a single enantiomer, unless otherwise stated; enantiomeric mixtures of each compound are designated as "a mixture of the enantiomers" of formula (I), (II) or (III) respectively. "A single enantiomer" means one of the individual enantiomers of a given compound substantially free of the other.

It will be further appreciated that for use in medicine a salt of a compound (I) should be pharmaceutically acceptable. Examples of pharmaceutically acceptable salts include inorganic and organic acid addition salts such as hydrochloride, hydrobromide, sulphate, phosphate, acetate, fumarate, maleate, citrate, lactate, tartrate, methanesulphonate or similar pharmaceutically acceptable inorganic or organic acid addition salts. Other non-pharmaceutically acceptable salts e.g. oxalates, may be used for example in the isolation of final products and are included within the scope of this invention.

A single enantiomer of formula (I) may be prepared either from a corresponding mixture of enantiomers or from a resolved intermediate, according to the general methods known in the art. Thus in a further aspect the present invention provides a process for preparing an enantiomer of formula (I) which comprises:

(A) obtaining a single enantiomer of formula (I) from a corresponding mixture of enantiomers e.g. a racemic mixture, by conventional methods, for example:
(i) Separation of a mixture of the enantiomers of formula (I) or a derivative thereof by chromatography e.g. on a chiral HPLC column;
(ii) Separation of diastereoisomers of a chiral derivative (e.g. a chiral salt or amide) of a mixture of the enantiomers of formula (I) e.g. by crystallisation, or by chromatography;

(B) deprotection of a single enantiomer of formula (II);

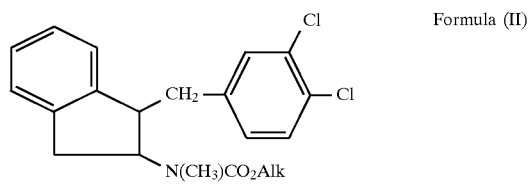

Formula (II)

wherein Alk is a $C_{1-4}$alkyl group, eg ethyl or t-butyl;
(C) reduction of a single enantiomer of formula (III):

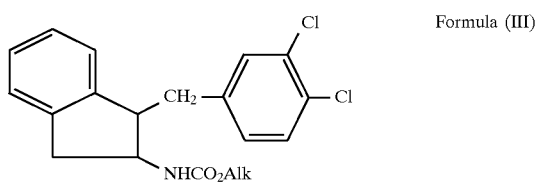

Formula (III)

wherein Alk is a $C_{1-4}$alkyl group eg methyl or ethyl;
followed if necessary or desired by converting a derivative of an enantiomer of formula (I) so obtained into an enantiomer of formula (I) itself e.g. by removal of any N-protecting group or facilitating group; conversion of a salt into the free base, and/or salt formation.

Separation according to process A(i) may be facilitated by first introducing a readily removable group into the methylamino moiety of a mixture of the enantiomers of formula (I). Suitable removable facilitating groups include those commonly used as N-protecting groups e.g. an alkoxycarbonyl group such as t-butoxycarbonyl. The resulting enantiomeric mixture can be applied to a chiral HPLC column and fractions containing the individual isomers collected. A facilitating group may be removed by standard methods such as acid hydrolysis.

In process A(ii) a chiral salt may be prepared for example by reaction of a mixture, such as a 1:1 racemate, of the enantiomers of formula (I) with an optically active acid. A mixture of diastereomeric amides may be prepared by reacting a mixture of the enantiomers of formula (I), with an optically active reagent such as S(+)-α-methoxyphenylacetic acid, in the form of a reactive derivative such as an acid chloride. The mixture of amides may be separated by conventional methods and then converted into the resolved amines by treatment with an excess of methyllithium, or by treatment with an excess of potassium t-butoxide in wet tetrahydrofuran as generally described in U.S. Pat. No. 5,149,714.

Deprotection of a compound of formula (II) according to process (B) may be carried out by conventional methods. Preferably the protecting group is tert-butoxycarbonyl, which may be cleaved using trifluoroacetic acid, in a solvent such as dichloromethane. An ethoxycarbonyl group may be removed by hydrolysis under basic conditions.

Reduction of a compound of formula (III) according to process (C) may be effected using a suitable reducing agent such as lithium aluminium hydride, preferably in an inert solvent such as tetrahydrofuran or diethyl ether.

It will be appreciated that when any of the processes described herein involve a reduction step it will generally be desirable to employ reducing agents and conditions which do not affect or disturb substituents which are intended to be retained in the final product. The choice of appropriate reducing agents and conditions will be readily apparent to the skilled practitioner. Thus, since Ar represents 3,4-dichlorophenyl it is preferable to avoid the use of lithium aluminium hydride under forcing (e.g. reflux) conditions.

A mixture of the enantiomers of formula (I) employed in process (A) may be prepared using methods analogous to processes (B) and (C) above, employing a mixture of the enantiomers of formula (II) or (III) respectively.

Processes (B) and (C) generally proceed with retention of the configuration of the starting material. It will therefore be appreciated that starting materials of the appropriate configuration i.e. cis should be employed.

The following processes for the preparation of compounds of formulae (II) and (III) may be applied to single enantiomers or mixtures thereof.

Compounds of formula (II) may be prepared by methylation of a compound of formula (III) for example using methyl halide in the presence of a base such as sodium hydride and in a suitable solvent e.g. dimethylformamide.

Compounds of formula (III) may be prepared by acylation of a corresponding compound of formula (IV):

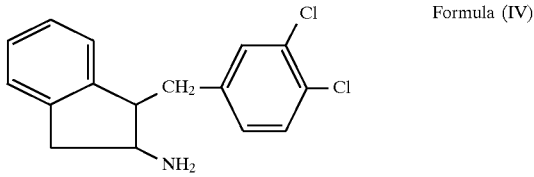

Formula (IV)

using for example an alkylhaloformate such as ethyl chloroformate, preferably in the presence of a tertiary amine such as triethylamine, or a carbonate such as di-tert-butyldicarbonate, in the presence of sodium hydroxide and a solvent such as dioxane.

The compound of formula (IV) may be prepared by reduction of a compound of formula (V):

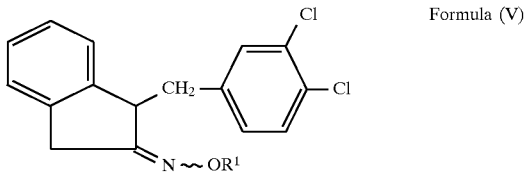

Formula (V)

wherein $R^1$ is hydrogen, $C_{1-4}$alkyl or phenyl$C_{1-4}$alkyl (eg benzyl); using a reducing agent such as lithium aluminium hydride, $NaBH_3(OCOCF_3)$ or preferably lithium borohydride and chlorotrimethylsilane in an inert solvent such as an ether, e.g. diethyl ether or tetrahydrofuran. In general this process gives predominantly the cis-form of the product. Preferably $R^1$ is $C_{1-4}$alkyl.

Reduction of a compound of formula (V) results in a mixture of enantiomers of formula (IV) which may be separated using standard procedures, e.g., by reaction with an optically active acid such as D (−) mandelic acid and separating the resulting diastereoisomers by crystallisation.

A compound of formula (V) may itself be prepared by reaction of a compound of formula (VI):

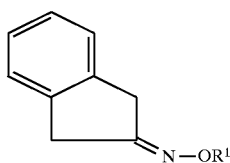

Formula (VI)

wherein R¹ is as hereinbefore defined; with a compound of formula (VII):

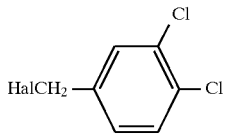

Formula (VII)

wherein Hal is a halogen atom, in the presence of lithium bis-(trimethylsilyl)amide in a solvent such as tetrahydrofuran.

Compounds of formulae (VI) and (VII) may be prepared using methods known in the literature.

An ischaemic event such as stroke results in disruption of the blood supply to the brain, depriving it of essential oxygen and glucose. A cascade of biochemical reactions ensues, a consequence of which is to permit the influx of calcium ions into the brain cells (neurons) via so-called Voltage Operated Calcium Channels (VOCCs) causing cell death. It is believed that agents which inhibit such calcium influx will minimise cell death and hence increase the potential for recovery.

The enantiomers of formula (I) have been found to exhibit high calcium influx blocking activity for example in neurons. The compounds may thus be referred to as neuronal calcium antagonists. As such the compounds are expected to be of use in therapy in treating conditions and diseases related to an accumulation of calcium in the brain cells of mammals, in particular humans. For example, the compounds are expected to be of use in the treatment of ischaemia including for example stroke; anoxia, due to causes including cardiac arrest and cardiac surgery; and traumatic head injury. They may also be of use in the treatment of migraine; pain; epilepsy; AIDS-related dementia; neurodegenerative diseases such as Alzheimer's disease and age-related memory disorders; mood disorders; and drug addiction withdrawal such as ethanol addiction withdrawal.

The enantiomers of formula (I) have also been found to inhibit nitric oxide synthase (NOS) and may be useful in treatment of conditions where such inhibition is beneficial. Such conditions include neurodegenerative disease and CNS malfunction following ischaemic stroke or traumatic brain injury, migraine, neuralgia, chronic pain and neuropathic pain.

In a further aspect of the invention there is therefore provided a method of treatment of conditions or diseases related to (e.g. caused or exacerbated by) the accumulation of calcium in the brain cells of mammals which comprises administering to a subject in need thereof an effective amount of an enantiomer of formula (I) or a pharmaceutically acceptable salt thereof. Thus, for example, the present invention provides a method of treatment of ischaemia including for example stroke; anoxia or traumatic head injury which comprises administering to a subject in need thereof, an effective amount of an enantiomer of formula (I) or a pharmaceutically acceptable salt thereof. The invention also provides a method of treatment of migraine, pain, epilepsy, AIDS-related dementia, neurodegenerative diseases such as Alzheimer's disease, and age-related memory disorders, mood disorders and drug addiction withdrawal such as ethanol addiction withdrawal, which comprises administering to a subject in need thereof, an effective amount of an enantiomer of formula (I) or a pharmaceutically acceptable salt thereof.

The present invention also provides the use of an enantiomer of formula (I) or a pharmaceutically acceptable salt thereof in the manufacture of a medicament for the treatment of a condition or disease related to the accumulation of calcium in the brain cells of a mammal, e.g. as listed hereinabove.

Compounds of the present invention will preferably be of use in the treatment of ischaemic stroke.

For use in medicine, an enantiomer of formula (I) is usually administered in a standard pharmaceutical composition. The present invention therefore provides in a further aspect pharmaceutical compositions comprising an enantiomer of formula (I) or a pharmaceutically acceptable salt thereof and a pharmaceutically acceptable carrier or excipient.

An enantiomer of formula (I) may be administered by any convenient method for example by oral, parenteral, buccal, rectal or transdermal administration and the pharmaceutical compositions adapted accordingly.

An enantiomer of formula (I) and its pharmaceutically acceptable salts which are active when given orally can be formulated as liquids or solids, for example syrups, suspensions or emulsions, tablets, capsules and lozenges.

A liquid formulation will generally consist of a suspension or solution of the compound or pharmaceutically acceptable salt in a suitable liquid carrier(s) for example, ethanol, glycerine, non-aqueous solvent, for example polyethylene glycol, oils, or water with a suspending agent, preservative, flavouring or colouring agent.

A composition in the form of a tablet can be prepared using any suitable pharmaceutical carrier(s) routinely used for preparing solid formulations. Examples of such carriers include magnesium stearate, starch, lactose, sucrose and cellulose.

A composition in the form of a capsule can be prepared using routine encapsulation procedures. For example, pellets containing the active ingredient can be prepared using standard carriers and then filled into a hard gelatin capsule; alternatively, a dispersion or suspension can be prepared using any suitable pharmaceutical carrier(s), for example aqueous gums, celluloses, silicates or oils and the dispersion or suspension then filled into a soft gelatin capsule.

An enantiomer of the present invention may also be administered parenterally, by bolus injection or continuous infusion. Typical parenteral compositions consist of a solution or suspension of the compound or pharmaceutically acceptable salt in a sterile aqueous carrier or parenterally acceptable oil, for example polyethylene glycol, polyvinyl pyrrolidone, lecithin, arachis oil or sesame oil. Alternatively, the solution can be lyophilised and then reconstituted with a suitable solvent just prior to administration.

Both liquid and solid compositions may contain other excipients known in the pharmaceutical art, such as cyclodextrins.

Preferably the composition is in unit dose form such as a tablet, capsule or ampoule.

Each dosage unit for oral administration contains preferably from 1 to 250 mg (and for parenteral administration contains preferably from 0.1 to 60 mg) of a compound of the formula (I) or a pharmaceutically acceptable salt thereof calculated as the free base.

The daily dosage regimen for an adult patient may be, for example, an oral dose of between 1 mg and 500 mg, preferably between 1 mg and 250 mg, e.g. 5 to 200 mg or an intravenous, subcutaneous, or intramuscular dose of between 0.1 mg and 100 mg, preferably between 0.1 mg and 60 mg, e.g. 1 to 40 mg of the compound of the formula (I) or a pharmaceutically acceptable salt thereof calculated as the free base, the compound being administered 1 to 4 times per day. Alternatively the compounds of the invention may be administered by continuous intravenous infusion, preferably at a dose of up to 400 mg per day. Thus, the total daily dosage by oral administration will be in the range 1 to 2000 mg and the total daily dosage by parenteral administration will be in the range 0.1 to 400 mg. Suitably the compounds will be administered for a period of continuous therapy, for example for a week or more.

If desired a compound of formula (I) or a pharmaceutically acceptable salt thereof may be administered in combination or concurrently with one or more other therapeutic agents, for example a thrombolytic agent such as anistreplase, streptokinase or a tissue plasminogen activator; an excitatory amino acid antagonist such as an NMDA antagonists; a free radical inhibitor; or a calpain inhibitor.

BIOLOGICAL DATA

$Ca^{2+}$ Current Measurement

Cell preparations

Superior cervical ganglion neurons were isolated and cultured following a method modified from Marrion et al, Neurosci. Lett., 77, 55–60 (1987). Cells were plated onto laminin coated plastic tissue culture dishes and incubated at 37° C. until just prior to recording. Electrophysiological recordings were performed from 2 to 9 days after dissociation.

Solutions

The pipette (internal solution) contained in mM: CsCl, 130; HEPES, 10; EGTA, 10; $MgCl_2$, 4; ATP, 2; buffered to pH 7.2 with CsOH. Cells were bathed in a normal Tyrodes solution before establishment of whole cell recording when the bathing solution was changed to one allowing isolation of $Ca^{2+}$ currents. The external solution for recording $Ca^{2+}$ channel currents contained in mM: $BaCl_2$, 10; TEA-Cl, 130; glucose, 10; HEPES, 10; $MgCl_2$, 1; buffered to pH 7.3 with TEA-OH. Barium was used as the charge carrier as this assists in current isolation and calcium dependent inactivation of current is avoided. Compounds were dissolved in DMSO to make a 20 mM stock solution. At the highest drug concentration used the vehicle (0.1%) had no significant effect on $Ca^{2+}$ currents. All experiments were performed at 21° to 24° C. Whole cell currents were recorded using List EPC-7 amplifiers and stored, digitised for later analysis using PC based software similar to that described previously (Benham & Tsien, Journal of Physiology (1988), 404, 767–784).

Results $Ca^{2+}$ currents

Peak voltage gated $Ca^{2+}$ channel currents of up to 10 nA were recorded using 10 mM $Ba^{2+}$ as charge carrier. Currents were evoked from a holding potential of −80 mV to a test potential of 0 or +10 mV every 15 seconds. This test potential was at the peak of the current voltage relationship and assessing block at this point reduced any errors due to drifting holding potential. Some cells showed slow rundown of current as is commonly seen when recording $Ca^{2+}$ currents. The rundown rate was measured in control conditions and extrapolated through the time of drug application to derive a rundown corrected control value.

Once a constant calcium current had been recorded for 4 successive pulses (1 minute) 10 $\mu$M Nimodipine, a dihydropyridine, was applied to the cell to block L type calcium current. After three minutes 5 $\mu$M drug was coapplied with 10 $\mu$M Nimodipine for three minutes. Such drug application tested the block of the remaining, predominantly N type, calcium current. Under these conditions the compounds of Examples 1 and 2 gave, respectively, 95% and 99% inhibition of plateau $Ca^{2+}$ current.

In Vivo

Gerbil BCAO Model

Male Mongolian gerbils weighing between 60–80 g were anaesthetised with halothane, placed on a heated mat and the carotid arteries occluded for 6 min. After reperfusion, the animals were sutured and placed in an incubator for 2 hours to maintain body temperature during the acute recovery phase. The animals were then caged separately and on the 5th day after the day of surgery they were euthanased and the brains removed for histological analysis. The dosing protocol in these experiments was 15 $mg.kg^{-1}$ 30 minutes post-ischaemia then 5 $mg.kg^{-1}$ b.i.d. for 3 days. Injections were given via the i.p. route, and the vehicle was distilled water.

The test compounds described in Example 1 and Example 2 each produced a significant attenuation of the histological damage in the CA1 region of the hippocampus compared with that seen in the ischaemic vehicle-treated animals.

Mouse MCAO Model

Male CD1 mice weighing 25–29 g were anaesthetised with tribromoethanol, placed on a heat-pad and maintained at 37° C. The mid-cerebral artery was cauterised and divided via the intra-cranial route. On completion of surgery the mice were placed in an incubator for 2 hours to maintain body temperature during the acute recovery phase. On the 4th day the mice were euthanased and the brains removed for histological analysis. The dosing protocol in these experiments was 10 $mg.kg^{-1}$ 30 minutes post-ischaemia then 10 $mg.kg^{-1}$ b.i.d. for 3 days. Injections were given via the i.p. route, and the vehicle was distilled water.

The test compounds described in Example 1 and Example 2 each produced a significant attenuation of the histological damage in the cerebral cortex compared with that seen in the ischaemic vehicle-treated animals.

PHARMACEUTICAL FORMULATIONS

The following represent typical pharmaceutical formulations according to the present invention, which may be prepared using standard methods.

| IV Infusion | |
|---|---|
| Compound of formula (I) | 1–40 mg |
| Buffer | to pH ca 7 |
| Solvent/complexing agent | to 100 ml |
| Bolus Injection | |
| Compound of formula (I) | 1–40 mg |
| Buffer | to pH ca 7 |
| Co-Solvent | to 5 ml |

Buffer: Suitable buffers include citrate, phosphate, sodium hydroxide/hydrochloric acid.

Solvent: Typically water but may also include cyclodextrins (1–100 mg) and co-solvents such as propylene glycol, polyethylene glycol and alcohol.

| Tablet | |
|---|---|
| Compound | 1–40 mg |
| Diluent/Filler* | 50–250 mg |
| Binder | 5–25 mg |
| Disentegrant* | 5–50 mg |
| Lubricant | 1–5 mg |
| Cyclodextrin | 1–100 mg |

*may also include cyclodextrins

Diluent: e.g. Microcrystalline cellulose, lactose, starch
Binder: e.g. Polyvinylpyrrolidone, hydroxypropymethylcellulose
Disintegrant: e.g. Sodium starch glycollate, crospovidone
Lubricant: e.g. Magnesium stearate, sodium stearyl fumarate.

| Oral Suspension | |
|---|---|
| Compound | 1–40 mg |
| Suspending Agent | 0.1–10 mg |
| Diluent | 20–60 mg |
| Preservative | 0.01–1.0 mg |
| Buffer | to pH ca 5–8 |
| Co-solvent | 0–40 mg |
| Flavour | 0.01–1.0 mg |
| Colourant | 0.001–0.1 mg |

Suspending agent :e.g. Xanthan gum, microcrystalline cellulose
Diluent: e.g. sorbitol solution, typically water
Preservative: e.g. sodium benzoate
Buffer: e.g. citrate
Co-solvent: e.g. alcohol, propylene glycol, polyethylene glycol, cyclodextrin The invention is further illustrated by the following non-limiting Preparations and Examples:

Preparation 1
(±)E,Z-1-(3,4-Dichlorobenzyl)-2-indanone oxime-O-methyl ether

To a solution of 2-indanone oxime-O-methyl ether (5.05 g, 31 mmol) in dry tetrahydrofuran (250 ml) at −78° C. under argon was added lithium bis-(trimethylsilyl)amide (41 ml of a 1M solution in tetrahydrofuran, 41 mmol ) to afford a green solution. After 10 minutes 3,4-dichlorobenzyl chloride (7.34 g, 38 mmol) was added in one portion and the cooling bath removed. When the reaction mixture had reached room temperature, stirrring was continued for a further 30 minutes before pouring into a large excess of water and extracting with diethyl ether (3×100 ml). The combined organic extracts were dried over sodium sulfate and volatiles removed in vacuo. The residue was subjected to column chromatography on silica gel eluting with 10% diethyl ether in hexanes to afford the title compound as a yellow oil (8.04 g).

$^1$H Nmr (Major isomer)(CDCl$_3$) δ:3.14–3.18 (2H, m), 3.51 (2H, d, J=20 Hz), 3.97 (3H, s), 4.43 (1H, t, J=5 Hz), 6.60–7.23 (7H, m).

Preparation 2
Method A
(±)cis-1-(3,4-Dichlorobenzyl)-2-aminoindane

To a solution of lithium aluminium hydride (2.19 g, 58 mmol) in dry diethyl ether (100 ml) was added dropwise a solution of (±) E,Z-1-(3,4-dichlorobenzyl)-2-indanone oxime-O-methyl ether (8.04 g, 25 mmol) in diethyl ether (400 ml). The mixture was allowed to stir at room temperature for 18 h before careful addition of a minimum amount of water to quench the reaction. The precipitated aluminum salts were filtered off and solvents removed in vacuo. The residue was subjected to column chromatography on silica gel eluting with 5% ethanol in chloroform. Pooling of pure fractions containing the major faster running component afforded the title compound as an oil (2.11 g) which was converted to the HCl salt and crystallised to give a white solid. m.p.>198° C. dec. (from ethanol-diethyl ether).

$^1$H Nmr (HCl salt) (CDCl$_3$) δ:2.61 (1H, t, J=14 Hz), 3.13–3.25 (3H, m), 3.63 (1H, m), 4.02 (1H, m), 6.42 (1H, d, J=7 Hz), 7.03 (1H, t, J=7 Hz), 7.16 (2H, m), 7.30 (1H, d, J=7 Hz), 7.45 (1H, s), 7.60 (1H, d, J=7 Hz), 8.57 (3H, br.s)

Method B
To a slurry of lithium borohydride (9.91 g, 0.456 mol) in dry tetrahydrofuran (900 ml), under argon at −20° C., was added chlorotrimethylsilane (145 ml, 1.14 mol). The mixture was stirred at room temperature for 2 hours then cooled to −20° C. and treated dropwise with a solution of (±) E,Z-1-(3,4-dichlorobenzyl)-2-indanone oxime O-methyl ether (26.6 g, 83 mmol) in dry tetrahydrofuran (50 ml). Stirring was continued for 18 hours at room temperature before quenching with methanol (100 ml), and treatment with triethylamine (75 ml). Concentration in vacuo produced a pale yellow solid which was partitioned between ice-cold water (300 ml) and dichloromethane (400 ml). The aqueous layer was extracted with further portions of dichloromethane (4×100 ml) and the combined organic extracts were dried over sodium sulphate and concentrated in vacuo. The residue was subjected to column chromatography eluting with 5% ethanol in chloroform to afford the title compound as a pale yellow oil (12.2 g, 51%).

Preparation 3
(±) cis-1-(3,4-Dichlorobenzyl)-2-tert-butoxycarbonylaminoindane (±)cis-1-(3,4-Dichlorobenzyl)-2-aminoindane (1.29 g, 4.4 mmol, prepared as in Prep 2, method A) was dissolved in 1,4-dioxane (100 ml) and cooled to 0° C. Aqueous 3M NaOH (1.48 ml) and di-tert-butyldicarbonate (1.02 ml, 4.4 mmol) were added, and the reaction stirred at room temperature for 3 h before pouring into water and extracting with diethyl ether (3×100 ml). After drying over sodium sulfate, solvents were removed in vacuo and the residue recrystallised from ethanol/hexanes to afford the title compound as a white solid (1.65 g).

$^1$H Nmr (CDCl$_3$) δ:1.54 (9H, s), 2.68–2.81 (2H, m), 2.92 (1H, dd, J=7,15 Hz), 3.14 (1H, dd, J=7,15 Hz), 3.44–3.59 (1H, m), 4.47–4.53 (1H, m), 4.73 (1H, d, J=9 Hz), 6.81 (1H, d, J=7 Hz), 6.99 (1H, d, J=9 Hz), 7.08–7.26 (4H, m), 7.45 (1H, d, J=9 Hz).

(±) cis- 1-(3,4-dichlorobenzyl)-2-tert-butoxycarbonylaminoindane was also prepared using (±)cis-1-(3,4-dichlorobenzyl)-2-aminoindane prepared by Method B of Prep 2.

Preparation 4
(±) cis-1-(3,4-Dichlorobenzyl)-2-(N-methyl-N-tert-butoxycarbonylamino)indane To a suspension of sodium hydride (80% disp. in oil, 130 mg, 4.2 mmol) in dry N,N-dimethylformamide (6 ml) under nitrogen was added dropwise a solution of (±) cis-1-(3,4-dichlorobenzyl)-2-tert-butoxycarbonylaminoindane (1.65 g, 4.2 mmol) in N, N-dimethylformamide (10 ml). After stirring the mixture for 30 minutes at room temperature, iodomethane (0.28 ml, 4.5 mmol) was added dropwise and stirring continued for a further 1 h. The reaction mixture was then poured into a large excess of sat. ammonium chloride and extracted with diethyl ether (3×40 ml). The combined organic extracts were dried over sodium sulfate and concentrated in vacuo. The residue was subjected to column chromatography on silica gel eluting with 10% diethyl ether in hexanes to afford the title compound as a colourless oil (1.02 g).

$^1$H Nmr (CDCl$_3$) δ:1.45 (9H, s), 2.65 (3H, s), 2.70–2.91 (2H, m), 3.04 (1H, dd, J=6,15 Hz), 3.18 (1H, dd, J=7,15 Hz), 3.64 (1H, m), 4.98 (1H, br.s), 6.78 (1H, d, J=7 Hz), 7.02–7.29 (5H, m), 7.37 (1H, d, J=9 Hz).

Preparation 5

(±)cis-1-(3,4-Dichlorobenzyl)-2-methylaminoindane

To a solution of (±) cis-1-(3,4-dichlorobenzyl)-2-(N-methyl-N-tert-butoxycarbonyl-amino)indane (1.016 g, 2.5 mmol) in dichloromethane (20 ml) at 0° C. was added trifluoroacetic acid (4 ml) dropwise. The solution was then stirred at room temperature for 2 h, poured into saturated aqueous NaHCO$_3$ (150 ml) and extracted with dichloromethane (3×30 ml). The combined organic phases were dried over sodium sulfate, and concentrated in vacuo. The residue was subjected to column chromatography on silica eluting with 5% ethanol in chloroform to afford the title compound as a colourless oil (585 mg) which was converted to the HCl salt and crystallised to afford a white solid. m.p.>245° C. dec. (from ethanol-diethyl ether).

$^1$H Nmr (HCl salt)(CDCl$_3$)δ:2.48 (1H, t, J=14 Hz), 2.72 (3H, s), 3.23 (3H, m), 3.61 (1H, m), 3.94 (1H, q, J=7 Hz), 6.21 (1H, d, J=7 Hz), 7.00 (1H, t, J=7 Hz), 7.09 (1H, d, J=7 Hz), 7.19 (1H, t, J=7 Hz), 7.30 (1H, d, J=7 Hz), 7.38 (1H, s), 7.58 (1H, d, J=7 Hz), 9.66 (2H, br.s)

Preparation 6

(+) cis-1-(3,4-Dichlorobenzyl)-2-aminoindane and (−) cis-1-(3,4-Dichlorobenzyl)-2-aminoindane A solution of (±) cis-1-(3,4-dichlorobenzyl)-2-aminoindane (7.58 g, 0.026 mol) in ethanol (60 ml) was treated with D (−) mandelic acid (3.95 g, 0.026 mol). The solution was warmed on a steam bath and then concentrated in vacuo. The resulting foam was dissolved in diethyl ether then concentrated on a steam bath and allowed to crystallise to give the D (−) mandelic acid salt as a white solid (5.3 g) from which (−) cis-1-(3,4-dichlorobenzyl)-2-aminoindane was liberated.

Specific optical rotation=−50.2 (chloroform, c=0.6, 20° C.)

Enantiomeric purity=90.3% based on chiral HPLC analysis (Chiralpak AD column eluting with 90/10 hexane/ethanol +0.1% DEA).

Evaporation of the mother liquor afforded a foam (6.3 g) from which (+) cis-1-(3,4-dichlorobenzyl)-2-aminoindane was liberated.

Enantiomeric purity=89.5% based on chiral HPLC analysis (Chiralpak AD column eluting with 90/10 hexane/ethanol +0.1% DEA).

EXAMPLES 1 AND 2

(+)cis-1-(3,4-Dichlorobenzyl)-2-methylaminoindane Hydrochloride (E1)
(−)cis-1-(3,4-Dichlorobenzyl)-2-methylaminoindane Hydrochloride (E2)

To a solution of S-(+)-α-methoxyphenylacetic acid (2.41 g, 14.5 mmol) in dichloromethane (100 ml) was added thionyl chloride (15 ml) and the mixture heated at reflux for 90 minutes. On cooling, the mixture was concentrated in vacuo. The residue was then dissolved in dichloromethane (50 ml) and added to a mixture of (±)cis-1-(3,4-dichlorobenzyl)-2-methylaminoindane (3.7 g, 12.1 mmol prepared from (±)cis-1-(3,4-dichlorobenzyl)-2-aminoindane obtained using Preparation 2, Method A), dichloromethane (50 ml) and 1M aq. sodium hydroxide (100 ml). The two phase mixture was then stirred vigorously for 1 h. The layers were then separated and the aqueous phase extracted with dichloromethane. The combined organic phases were washed with brine, dried over sodium sulfate and concentrated in vacuo to afford a 50:50 mixture of two diastereomers which were readily separated by column chromatography on silica gel, eluting with 50% diethyl ether in 60°–80° C. petrol.

The faster eluting diastereomer (2.2 g, 4.8 mmol) was dissolved in dry tetrahydrofuran (175 ml) and treated with potassium tert-butoxide (22 g), and water (0.37 ml). The mixture was then stirred vigorously for 45 minutes. After filtering off the solid material, the mixture was concentrated in vacuo and the residue partitioned between diethyl ether and water. The organic layer was dried over sodium sulfate and concentrated in vacuo. The residue was subjected to column chromatography on silica gel eluting with 5% ethanol in chloroform to afford a brown oil which was converted to the HCl salt and crystallised to afford (+)cis-1-(3,4-dichlorobenzyl)-2-methylaminoindane hydrochloride (E1) (297 mg) as a white solid. m.p.>250° C. dec. (from methanol-diethyl ether).

Specific optical rotation=30 160° (chloroform, c=1, 24° C.)

The slower eluting diastereomer (2.2 g, 4.8 mmol) was dissolved in dry tetrahydrofuran (175 ml) and treated with potassium tert-butoxide (22 g), and water (0.37 ml). The mixture was then stirred vigorously for 45 minutes. After filtering off the solid material, the mixture was concentrated in vacuo and the residue partitioned between diethyl ether and water. The organic layer was dried over sodium sulfate and concentrated in vacuo. The residue was subjected to column chromatography on silica gel eluting with 5% ethanol in chloroform to afford a brown oil which was converted to the HCl salt and crystallised to afford (−)cis-1-(3,4-dichlorobenzyl)-2-methylaminoindane hydrochloride (E2) (250 mg) as a white solid. m.p.>250° C. dec. (from methanol-diethyl ether).

Specific optical rotation=−159° (chloroform, c=1, 24° C.)

Additional Preparation of Examples 1 and 2
(+)cis-1-(3,4-Dichlorobenzyl)-2-methylaminoindane Hydrochloride (E1)
(−)cis-1-(3,4-Dichlorobenzyl)-2-methylaminoindane Hydrochloride (E2)

(±)cis-1-(3,4-Dichlorobenzyl)-2-methylaminoindane (7.49 g) was prepared from (±)cis-1-(3,4-dichlorobenzyl)-2-aminoindane (Preparation 2, Method B, 13.95 g) as described in Preparations 3–5 , and then converted into the single enantiomers (+)cis-1-(3,4-dichlorobenzyl)-2-methylaminoindane hydrochloride(E1) and (−)cis-1-(3,4-dichlorobenzyl)-2-methylaminoindane hydrochloride(E2) as described above. In each case chiral purity was greater than 99.5% as judged by chiral HPLC analysis (Column: CHIRALPAK AD; Eluent: 99/1 hexane/ethanol+0.1% DEA). The level of other impurities was<0.3% as judged by HPLC (Column: Merck RP—Select B. Eluent A: 0.1% TFA in water; Eluent B 0.1% TFA in acetonitrile; Eluent composition increased linearly from 5%B to 80% B over 40min. and then held at 80% B for a further 10 min).

The enantiomers of Examples 1 and 2 may also be prepared from the enantiomeric products of Preparation 6, using methods analogous to those described in Preparations 3, 4,and5.

We claim:

1. A single enantiomer of formula (I):

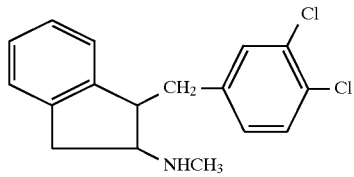

Formula (I)

or a salt thereof.

2. (+)cis-1-(3,4-dichlorobenzyl)-2-methylaminoindane or a salt thereof.

3. (−)cis-1-(3,4-dichlorobenzyl)-2-methylaminoindane or a salt thereof.

4. A compound according to any of claim 1 which is a hydrochloride salt.

5. An enantiomer according to any of claim 1 which contains less than 10% of the opposite enantiomer.

6. An enantiomer according to claim 5 which contains less than 1% of the opposite enantiomer.

7. A process for preparing a single enantiomer of formula (I), of claim 1, or a salt thereof which comprises (A) Obtaining a single enantiomer of formula (I) from a corresponding mixture of enantiomers by:
   (i) Separation of a mixture of the enantiomers of formula (I), of claim 1, or a derivative thereof by chromatography; or
   (ii) Separation of diastereoisomers of a chiral derivative of a mixture of the enantiomers of formula (I): or (B) deprotection of a single enantiomer of formula (II);

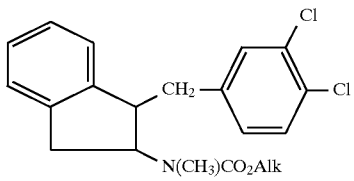

Formula (II)

wherein Alk is a $C_{1-4}$ alkyl group, eg ethyl or t-butyl: or (C) reduction of a single enantiomer of formula (III):

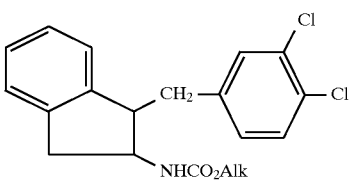

Formula (III)

wherein Alk is a $C_{1-4}$ alkyl group eg methyl or ethyl:

followed if necessary by converting a derivative of an enantiomer of formula (I) so obtained into an enantiomer of formula (I) itself: conversion of a salt into the free base, and/or salt formation.

8. A process according to claim 7 wherein the diastereoisomers are amide derivatives of formula (I).

9. A pharmaceutical composition comprising an enantiomer of claim 1 or a pharmaceutically acceptable salt thereof and a pharmaceutically acceptable carrier or excipient.

10. A method of treatment of a condition or disease related to the accumulation of calcium in the brain cells of a mammal which comprises administering to a subject in need thereof an effective amount of an enantiomer of any of claim 1 or a pharmaceutically acceptable salt thereof.

* * * * *